United States Patent
Sarode et al.

(10) Patent No.: US 11,433,026 B2
(45) Date of Patent: Sep. 6, 2022

(54) NANOPARTICLE-INDUCED FUSOGENICITY BETWEEN LIPOSOME AND ENDOSOME MEMBRANES FOR TARGETED DELIVERY THROUGH ENDOSOMAL ESCAPE

(71) Applicant: Rhode Island Council on Postsecondary Education, Warwick, RI (US)

(72) Inventors: Ashish Sarode, North Kingston, RI (US); Ruchi Verma, South Attleboro, MA (US); David Worthen, Kingston, RI (US); Ruitang Deng, Old Lyme, CT (US)

(73) Assignee: University of Rhode Island Board of Trustees, Kingston, RI (US)

( * ) Notice: Subject to any disclaimer, the term of this patent is extended or adjusted under 35 U.S.C. 154(b) by 0 days.

(21) Appl. No.: 15/943,538

(22) Filed: Apr. 2, 2018

(65) Prior Publication Data

US 2019/0105271 A1    Apr. 11, 2019

(51) Int. Cl.
*A61K 9/127* (2006.01)
*A61K 47/02* (2006.01)
(Continued)

(52) U.S. Cl.
CPC ........ *A61K 9/1271* (2013.01); *A61K 31/7088* (2013.01); *A61K 47/02* (2013.01);
(Continued)

(58) Field of Classification Search
CPC .. A61K 9/1271; A61K 31/7088; A61K 47/26; A61K 47/186; A61K 47/20;
(Continued)

(56) References Cited

U.S. PATENT DOCUMENTS 10,702,474 B2 *   7/2020   Sailor ................. A61P 31/04
2004/0072231 A1 * 4/2004   Mirkin ................ C12Q 1/6816
                                                435/6.12
(Continued)

FOREIGN PATENT DOCUMENTS

EP         1781 593       * 12/2005
WO       2017008059 A1      1/2017

OTHER PUBLICATIONS

Wu. G., et al in J. Am.Chem.Soc 130, pp. 8175-8177, 2008.*
(Continued)

*Primary Examiner* — Gollamudi S Kishore
(74) *Attorney, Agent, or Firm* — Milstein Zhang & Wu LLC; Duan Wu, Esq.

(57) ABSTRACT

The disclosure provides compositions and methods of use of formulations effective for the delivery of biologically active molecules and materials, including therapeutic and diagnostic agents, and combinations thereof, to cells, tissues, and living organisms. More particularly, the present invention is related to the incorporation of hydrophobic nanoparticles, such as hydrophobic metal nanoparticles, into the membranes of vesicular delivery vehicles. These hydrophobic nanoparticles enhance the endosomal membrane fusogenicity of the formulations through the promotion of inverted hexagonal phase formation in the lipid bilayers of the vesicular delivery vehicles. As a result, the vesicular delivery vehicles more readily fuse with the endosomal membranes, leading to enhanced endosomal escape of the vesicular delivery vehicle and its contents, thereby facilitating the delivery of the biologically active molecules and materials incorporated within the vesicular delivery vehicles to their sites of action.

20 Claims, 10 Drawing Sheets

(51) Int. Cl.
    *A61K 47/20* (2006.01)
    *A61K 47/18* (2017.01)
    *A61K 31/7088* (2006.01)
    *C12N 15/113* (2010.01)
    *A61K 47/26* (2006.01)

(52) U.S. Cl.
    CPC ............ *A61K 47/186* (2013.01); *A61K 47/20* (2013.01); *A61K 47/26* (2013.01); *C12N 15/113* (2013.01); *C12N 2310/14* (2013.01); *C12N 2320/32* (2013.01)

(58) Field of Classification Search
    CPC .. A61K 47/02; C12N 15/113; C12N 2310/14; C12N 2320/32
    See application file for complete search history.

(56) References Cited

U.S. PATENT DOCUMENTS

| | | | | |
|---|---|---|---|---|
| 2012/0095387 | A1* | 4/2012 | Malecki | G01N 33/56966 604/20 |
| 2015/0265708 | A1* | 9/2015 | Manoharan | A61K 9/1272 424/283.1 |

OTHER PUBLICATIONS

E. Seto et al., "When cell biology meets development: endocytic regulation of signaling pathways" Genes & Development, 16:1314-1336 (2002).

S. Guo et al., "Nanoparticles Escaping RES and Endosome: Challenges for siRNA Delivery for Cancer Therapy," J of Nanomaterials, V 2011, Article ID 742895 (2011).

A. Liapis et al., "MLN64 Transport to the Late Endosome Is Regulated by Binding to 14-3-3 via a Non-canonical Binding Site," PLoS One 7(4): e34424 (2012).

M. Jovic et al., "The early endosome: a busy sorting station for proteins at the crossroads," Histol Histopathol. 25(1):99-112(2010).

A. Varkouhi et al., "Endosomal escape pathways for delivery of biologicals," J of Controlled Release 151:220-228 (2011).

J. Szule et al., "The Effects of Acyl Chain Length and Saturation of Diacylglycerols and Phosphatidylcholines on Membrane Monolayer Curvature," Biophysical J. 83:977-984 (2002).

R. Epand et al., "Promotion of hexagonal phase formation and lipid mixing by fatty acids with varying degrees of unsaturation," Chem Phys Lipids, 57 (1):75-80 (1991).

J.M. Seddon et al., "Inverse micellar phases of phospholipids and glycolipids," Physical Chemistry Chemical Physics (2):4485-4493 (2000).

Y. Chen et al., "Controlled Release from Bilayer-Decorated Magnetoliposomes via Electromagnetic Heating," ACS Nano, 4(6):3215-3221 (2010).

X. An et al., "Smart Photothermal-Triggered Bilayer Phase Transition in AuNPs-Liposomes to Release Drug," Langmuir 29:1061-1068 (2013).

H.S. Wi et al., "Interfacial energy consideration in the organization of a quantum dot-lipid mixed system," J Phys: Condens. Matter 20:494211 (2008).

R. C. Van Lehn et al., "Lipid tail protrusions mediate the insertion of nanoparticles into model cell membranes," Nature Communications, DOI: 10.1038/ncomms5482 (2014).

M. R. Rasch et al., "Hydrophobic Gold Nanoparticle Self-Assembly with phosphatidylcholine Lipid: Membrane-Loaded and Janus Vesicles," Nano Lett. 10:3733-3739 (2010).

* cited by examiner

NANOPARTICLE-INDUCED FUSOGENICITY BETWEEN LIPOSOME AND ENDOSOME MEMBRANES FOR TARGETED DELIVERY THROUGH ENDOSOMAL ESCAPE

CROSS-REFERENCE TO RELATED APPLICATIONS

This application claims priority to and the benefit of U.S. provisional patent application Ser. No. 62/479,753, filed Mar. 31, 2017, which application is incorporated herein by reference in its entirety.

FIELD OF INVENTION

The present invention relates to vesicular delivery vehicles that deliver therapeutic and diagnostic agents into living cells, more specifically, liposomes incorporated with nanoparticles for quicker and easier endosomal escape of the liposomes and their contents.

BACKGROUND OF THE INVENTION

Biological drugs, or biologics, such as oligonucleotides, proteins, peptides, enzymes, plasmid DNA (pDNA), small interfering RNA (siRNA), and antibodies, are effective and typically target-specific agents for the prevention, palliation, and treatment of disease. These biologically active compounds may have therapeutic targets in the cytoplasm, in the nucleus, or on the surface of cellular structures, membranes, and organelles. Accordingly, there is strong and ongoing interest in their clinical development. Despite their therapeutic potential, however, the effective pharmaceutical formulation and targeted delivery of these agents to their cellular sites of action remains a significant challenge. If administered naked, these large, often charged, typically hydrophilic molecules face many hurdles before they reach their target site of action, such as rapid renal clearance, enzymatic degradation, opsonization, reticuloendothelial system (RES) uptake and metabolism, insufficient tissue and cell internalization, and immunosensitization, as well as endosomal degradation. Hence, in order to use these drugs therapeutically, it is necessary to develop vehicles or formulations for their efficient delivery to their site of action while protecting them from endosomal degradation (Wang, J. et al. *The AAPS Journal* 2010, 12(4):492-503).

The development of methods to facilitate the escape of these formulations from endosomes, wherein the rapid enzymatic and chemical degradation of polynucleotides and other biologics and materials would otherwise negate their therapeutic activity, has been recognized as a significant hurdle to their development as therapeutic agents. The endosomal uptake pathway is known to be a rate-limiting barrier to the intracellular delivery and activity of biologics drugs and formulations thereof, as these materials often become trapped in endosomal vesicles, where they are enzymatically and chemically degraded (El Ouahabi et al. *FEBS Letters* 1997, 414(2):187-192; and Shete et al. *J Nanosci Nanotechnol.* 2014, 14(1):460-74). Indeed, in addition to protecting polynucleotides and other biologic therapeutics from destruction while within the endosome, a reliable means for promoting their escape from the endosome is perhaps the most rate-limiting step for the expression of their biological activity and their ultimate development as therapeutic agents. Thus, there is a need for effective strategies and versatile formulation methods that facilitate endosomal escape after being taken up through endocytosis and enhance the cellular, cytosolic, and site-specific bioavailability of bioactive molecules, including biologics, as well as more traditional, small molecule drugs (Dominska et al. *J Cell Sci* 2010, 123:1183-1189; Varkouhi et al. *J Controlled Release* 2011, 151(3):220-8). The present invention describes novel and non-obvious methods that address this need.

In the case of polynucleotides, a number of methods and approaches for facilitating the endosomal escape of polynucleotides, such as siRNA and pDNA, and polynucleotide formulations, have been reported. These include methods closely modeled upon bacterial and viral pathogenesis and microbial effects on biological membranes, such as those mediated by pore formation, pH modification, and membrane fusion (Varkouhi et al., supra). Protein- and peptide-based drug delivery systems, both pH-dependent and independent, have been assessed for their capacity to promote membrane fusion and the endosomal escape and intracellular delivery of polynucleotides, with varying degrees of success. Cationic peptides have figured prominently in this approach due to their tendency to electrostatically interact with and condense polyanionic polynucleotides.

Lipids, lipid complexes, lipoplexes, and liposomal delivery systems have been widely used as carriers for nucleic acid-based and other biologic drugs because of their favorable formulation characteristics, such as biocompatibility, biodegradability, spontaneous self-assembly, ease of large-scale production, and suitability for clinical applications.

Cationic lipids and other surface-active agents have been assessed as delivery aids and endosomal escape promoters, although the cytotoxicity of many cationic peptides and surfactants may limit their clinical utility (Sarisozen, et al., *Current Pharmaceutical Biotechnology* 2016, 17(8):728-740; Pozzi et al., *Biochimica et Biophysica Acta, Biomembranes* 2014, 1838(3):957-967; Musacchio, et al., *Front. Biosci.* 2011, 16:1388-412; Heyes, et al., *J Control Release* 2005, 107 (2):276-87; and Semple, et al., *Nat Biotechnol* 2010, 28 (2):172-6).

Other types of lipids, including fatty acids, have been employed as polynucleotide and other biologics carrier molecules, alone or in combination, as complexes or lipoplexes. Various aspects of the interaction, including effects of acyl chain length, degree of unsaturation, and chemical isosteres on membrane curvature and phase have been examined in an effort to optimize endosomal escape and transfection efficiency (Majzoub et al., *J of Physical Chemistry B* 2016, 120(26):6439-6453; Epand et al., *Chem Phys Lipids* 1991, 57 (1):75-80; Szule et al., *Biophys J* 2002, 83 (2):977-84; Prades et al., *J Lipid Res* 2003, 44 (9):1720-7; and Majzoub et al., *J of Med Chem* 2007, 50(18):4269-78).

Some of the barriers to the path of efficient delivery of polynucleotide- and other biologic-based drugs, as well as small molecule drugs, to their sites of action have been addressed using liposomal delivery systems. For instance, the stability and plasma half-life of liposomes may be enhanced by adding neutral lipids, cholesterol, and polyethylene glycol (PEG) to the lipid formulation. The neutral lipids stabilize the liposomal bilayer by reducing repulsion between similar charges. Similarly, cholesterol embeds in the hydrophobic domains of the bilayer and enhances structural rigidity and also facilitates cellular uptake by improving endosomal internalization. PEG chains extend out of the lipid bilayer and provide a shield of steric hindrance on the surface of the liposome, which reduces interactions with opsonins and subsequent RES uptake. However, PEG chains also interfere with cellular uptake and endosomal escape. Hence, transient PEG coating strategies have been utilized, wherein exchangeable or reducible PEG linkages such as PEG-ceramide, disulfide-PEG, and orthoester-PEG lipids are used (Romberg et al., *Pharm Research* 2008, 25 (1):55-71). Moreover, the attachment of targeting ligands at the distal end of PEG moieties has improved cell-specific uptake.

From among these strategies, the fusion of the liposomal and endosomal membranes and the subsequent release of the liposomal cargo into the cytosol have been investigated (Heyes et al, *J Control Release* 2005, 107 (2):276-87). This membrane fusion occurs via inverted hexagonal (HII) phase formation between liposomal and endosomal bilayers. The HII phase formation can be enhanced by increasing the negative interfacial curvature of the liposomal bilayer using lipids with appropriate critical packing parameters (Semple et al., *Nat Biotechnol* 2010, 28 (2):172-6). For instance, the use of lipids with higher unsaturation in their chains generates a kink that assists in HII phase formation by increasing negative interfacial curvature (Epand et al, *Chem Phys Lipids* 1991, 57 (1):75-80; Prades et al., *J Lipid Res* 2003, 44 (9):1720-7; and Szule et al., *Biophys J* 2002, 83 (2):977-84). A packing frustration is generated in the hydrophobic domains of the lipids while the HII phase is being formed due to the creation of voids around the hydrophilic channels of the HII phase (Seddon et al., *Physical Chemistry Chemical Physics* 2000, (2):4485-4493).

Pharmaceutical research, in both academia and industry, is increasingly focused on the development of biotechnology-derived and genetically engineered nucleic acid based drugs such as pDNA, siRNA, shRNA, miRNA, antisense, and antigene oligonucleotides as potential therapeutics. These molecules can be highly target-specific, potent and used for treating various life-threatening ailments. However, many are very hydrophilic, are of high molecular weight, are often chemically- and enzymatically unstable, and are highly charged molecules. As stated previously, if administered naked, these molecules face many hurdles before they reach their target site of action, such as rapid renal clearance, serum degradation, opsonization, RES uptake and metabolism, insufficient tissue and cell internalization, and endosomal degradation, as well as immunosensitization. Hence, in order to use these drugs therapeutically, it is necessary to develop vehicles for their efficient delivery to their sites of action, which includes the capacity to promote their escape from endosomes. Among various potential formulation methods, the use of self-assembling lipids and polymers in order to produce vesicular delivery vehicles such as liposomes and polymersomes has proven to be one of the successful and feasible approaches. However, despite many efforts in the development of this type of delivery vehicle, endosomal degradation of their therapeutic cargo remains a significant limitation to their utility and effectiveness. Hence, there is a pressing need to develop novel techniques to promote endosomal escape of biologics before they are degraded in the endosome. The present invention addresses this need.

SUMMARY OF THE INVENTION

The present invention relates to compositions and methods for the delivery of biologically active molecules as a payload in a vesicular vehicle to cellular organelles, cells, tissues, and organs of a biological subject, preferably living, with enhanced biological activity of these molecules. More particularly, the present invention relates to compositions and methods for such delivery through the use of vesicular delivery vehicles that contain hydrophobic nanoparticles in their membranes. The present invention provides a novel method for increasing the fusogenicity of the membrane of vesicular delivery vehicles to endosomal membrane. More particularly, the inclusion of hydrophobic nanoparticles in the vesicular membranes induces inverted hexagonal phase formation therein, which enhances or promotes inter-membrane fusion between the vesicular membrane and the endosomal membrane in living cells, the subsequent escape of the vesicles and their biologically active payload or cargo from the endosome and into the cytosol, and ultimately, the delivery of biologically active molecules to their sites of action.

In preferred embodiments, a biologically active agent, such as a polynucleotide or a peptide, is encapsulated within the aqueous core of the vesicle such that the biologically active agent in the vesicle is protected from enzymatic degradation, such as by a nuclease or a protease, and the hydrophobic nanoparticles (NPs) are incorporated within the membrane of the vesicle such that the hydrophobic NPs enhance the fusogenicity of the vesicle membrane with the endosomal membrane. By "enhancing" or "enhanced" fusogenicity, it is referring to improvement in at least one factor that makes the desired fusion event occur more easily or more likely under the default conditions, e.g., normal physiological conditions. Specifically, the fusion event might occur sooner, faster, or at a lower energy threshold.

In one aspect, the present invention provides vesicles comprising: (a) one or more biologically active or therapeutic agents; (b) one or more types of cationic lipids; (c) one or more types of non-ionic lipids; and (d) one or more types of hydrophobic NPs. The vesicle has a membrane composed of (b) and (c), with (d) embedded or otherwise incorporated therein. The membrane defines a hollow core space where (a) is loaded, typically in a solution. Examples of such vesicles include different types of liposomes: e.g., multilamellar and unilamellar liposomes. Optionally, the vesicle membrane may further include amphiphilic block copolymers similar to those that make up a polymersome. Due to similarities between the polymersome and the liposome, and to the extent aspects of the present invention apply similarly to polymersome, coverage of corresponding polymersome embodiments is contemplated by the present invention.

More particularly, in one embodiment, the present invention provides liposomes comprising (a) a nucleic acid or polynucleotide-based molecule, such as plasmid DNA (pDNA) or small interfering RNA (siRNA); (b) a cationic lipid comprising from about 10 mol % to about 100 mol % of the total lipid present in the liposome; (c) a non-ionic lipid comprising from about 0.1 mol % to about 90 mol % of the total lipid present in the liposome; (d) an anionic lipid comprising from about 0.1 mol % to about 90 mol % of the total lipid present in the liposome; and (e) hydrophobic NPs, such as gold or silver hydrophobic nanoparticles (AuNPs or AgNPs) incorporated into the liposomal membranes at a ratio ranging from about 1,000:1 to about 20,000:1 (lipid molecules:NPs).

Without any hydrophobic NPs inside the liposomal bilayer, escape of the active agents or therapeutic agents from the endosome into the cytosol would be inefficient, thereby showing lower transfection efficiency. A method of enhancing the endosomal escape and delivery of these biologically active agents into the cytosol and to their sites of action is effected by promoting membrane fusogenicity via increasing the HII phase forming tendency of the liposomal bilayer through incorporating hydrophobic NPs into the liposomal bilayer.

In some embodiments, the incorporation of hydrophobic NPs inside the bilayer leads to a decrease in the HII phase transition temperature ranging from about 1 to about 20° C.: e.g., by about 2° C., 5° C., and 10° C.

In preferred embodiments, the use of the aforementioned hydrophobic NPs-containing liposomes for the delivery of biologically active agents leads to higher polynucleotide transfection efficiency, ranging from about 10% to about 10-fold or more, in the target cells as compared to that achieved using non-NPs-containing liposomes (i.e., liposomes that do not contain hydrophobic NPs in their bilayers).

BRIEF DESCRIPTION OF THE DRAWINGS

FIGS. 1A-1E show the chemical structures of the types of materials employed and FIG. 1F shows a schematic of the types of liposomes produced as examples illustrating the invention. The hydrophobic gold and silver nanoparticles (AuNPs and AgNPs), derivatized at the surface with hydrophobic chains of dodecanethiol, are shown in FIGS. 1A and 1B, respectively. The chemical structures of the cationic lipid 1,2-di-O-octadecenyl-3-trimethylammonium propane-chloride salt (DOTMA), the non-ionic lipid 1,2-distearoyl-sn-glycero-3-phosphocholine (DSPC), and the anionic lipid 1,2-dihexadecanoyl-sn-glycero-3-phospho-L-serine-sodium salt (DPPS), are shown in FIGS. 1C, 1E, and 1E, respectively.

DETAILED DESCRIPTION OF THE INVENTION

Unless otherwise noted, technical terms are used according to conventional usage.

As used in the specification and claims, the singular form "a", "an", or "the" includes plural references unless the context clearly dictates otherwise. For example, the term "a nanoparticle" includes a plurality of nanoparticles including mixtures thereof.

As used herein, "about" means within plus or minus 10%. For example, "about 1" means "0.9 to 1.1", "about 2%" means "1.8% to 2.2%", "about 2% to 3%" means "1.8% to 3.3%", and "about 3% to about 4%" means "2.7% to 4.4%."

As used herein, the term "subject" refers to any animal (e.g., a mammal), including, but not limited to humans, non-human primates, rodents, canines, and the like, which is to be the recipient of a particular treatment. Typically, the terms "subject" and "patient" are used interchangeably herein in reference to a human subject. A "biological subject" further includes tissue samples, cell cultures, and other lab setups that involve one or more biological elements.

As used herein, the term "biologically active" or "bioactive" agent or molecule, refers to any agent or molecule that participates in or otherwise affects at least an aspect of a biological process.

Given the utility of liposomes, including nanoliposomes, as delivery vehicles for biologics such as polynucleotides and for small molecule drugs, a great deal of research and method development has gone into the development of customized liposomes, wherein their inverted hexagonal phase formation and endosomal membrane fusion may be optimized. The methods employed are diverse, and have included novel lipids, mixtures of lipids and other membrane components, tagged or ligand-bound liposomes, pH-sensitive systems, and lipid-particle fusates (Liu et al., *J of Nanomaterials* 2015, 541763; and Wang et al., *Adv Drug Deliv Rev* 2015, 87:68-80). Nevertheless, the inclusion of hydrophobic metal nanoparticles in the membranes of liposomal delivery vehicles in order to relieve packing frustration, induce inverted hexagonal phase formation, promote endosomal membrane fusion and endosomal escape, thereby optimizing the delivery of bioactive molecules, drugs, and biologics, including polynucleotides, to their intracellular targets, has not been reported, and is a novel and useful approach for promoting the endosomal escape and enhancing the biological activity of polynucleotides and other biologically active agents, as demonstrated in the present invention. And while there have been studies on how to encourage nanoparticles to spontaneously insert into cell membranes (Van Lehn et al., *Nature Communications* 2014, 5:4482), there has been no report of vesicle compositions that incorporate nanoparticles within its bilayer for the purpose of promoting membrane-to-membrane fusion.

Whereas in the present invention, while not wishing to be bound by this theory, it was hypothesized that the presence of free flowing hydrophobic nanoparticles (NPs) in the bilayers of liposomal delivery vehicles would increase their negative interfacial curvature as well as satisfy the packing frustration during HII phase formation by filling up the voids in the hydrophobic domains, thereby resulting in inverted hexagonal phase formation and facilitated endosomal escape. Hence, various hydrophobic metal NPs of different sizes and made of different metals were incorporated at different concentrations into the bilayers of model liposomal formulations containing siRNA and pDNA as model biologically active agents. The enhancement in membrane-to-membrane fusogenicity and subsequent increase in the biological activity and transfection efficiency of the biologically active agents contained in these NPs-incorporating liposomal vehicles was demonstrated in the present work.

The present invention is based on the discovery that vesicular delivery systems, such as liposomes, that contain hydrophobic NPs in their membrane bilayers, more effectively deliver biologically active agents, including biologicals and small molecule drugs, to their sites of action in cells than do analogous, non-NPs containing liposomes. The incorporation of NPs in these systems results in improved intra-cellular delivery and activity of biologically active agents, such as polynucleotides (e.g., pDNA and siRNA). In particular, as illustrated by the examples incorporated herein, the present invention provides hydrophobic NPs-containing liposomes wherein the NPs promote inverted hexagonal phase formation in vesicular and endosomal membranes, increase the fusogenicity of vesicular membranes with endosomal membranes, and enhance the endosomal escape of liposomes and liposome-encapsulated biologically active agents, thereby increasing the delivery of liposomes and these agents into the cytosol. This results in a significant increase in the cellular delivery and biological activity, including the transfection efficiency, of said agents.

EXAMPLES

Example 1

As shown in FIG. 1, numerous hydrophobic NPs, such as gold and silver NPs coated with various hydrophobic materials, such as dodecanthiol (commercially available from nanoComposix (San Diego, Calif., USA) with a diverse size range, including NPs with a mean diameter of 2, 4, and 5 nm, were incorporated into the bilayers of liposomes comprising: (a) a nucleic acid (e.g., pDNA or siRNA molecules) and perhaps other active agents encapsulated in the hydrophilic core; (b) a cationic lipid (e.g., DOTMA) comprising from about 50 mol % to about 100 mol % of the total lipid present in the liposome; and (c) a non-cationic lipid (e.g., DSPC) comprising from about 0.01 mol % to about 50 mol % of the total lipid present in the liposome. While the range of nanoparticles useful for practicing the present invention generally range from about 0.1 nm to about 20 nm in average diameter, a preferred range of average diameter is between about 0.1 nm to about 5 nm.

Figure 1A:
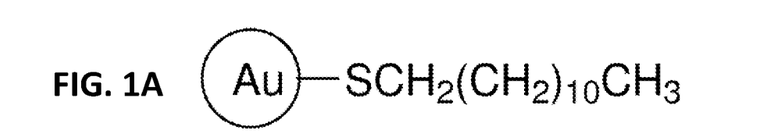
Figure 1B:
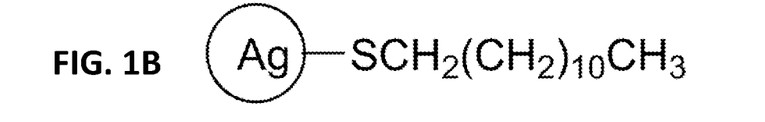
Figure 1C:
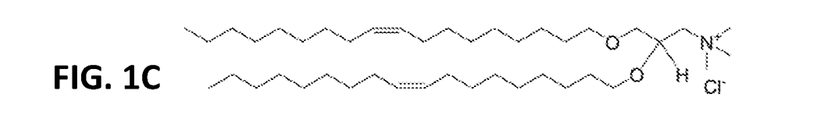
Figure 1D:
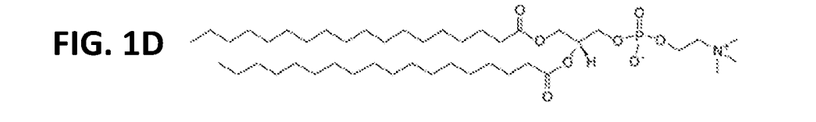
Figure 1E:
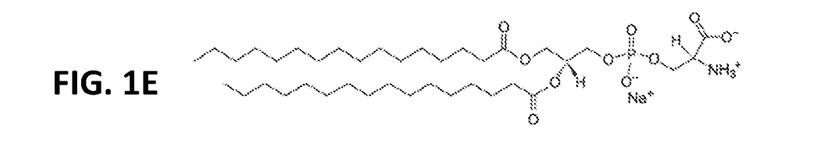
Figure 1F:
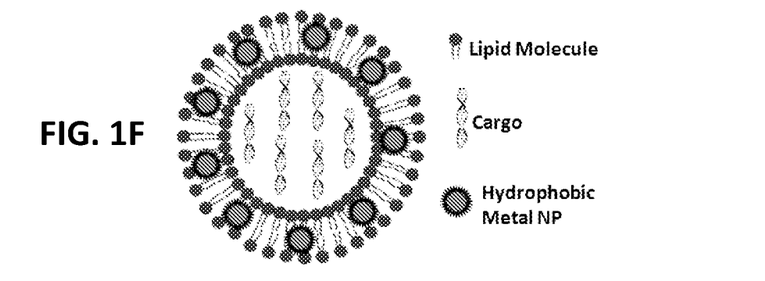
FIG. 1F shows the schematic of a representative liposome containing active agents or therapeutic agents inside the aqueous core and hydrophobic NPs in the bilayer.
Figure 2A:
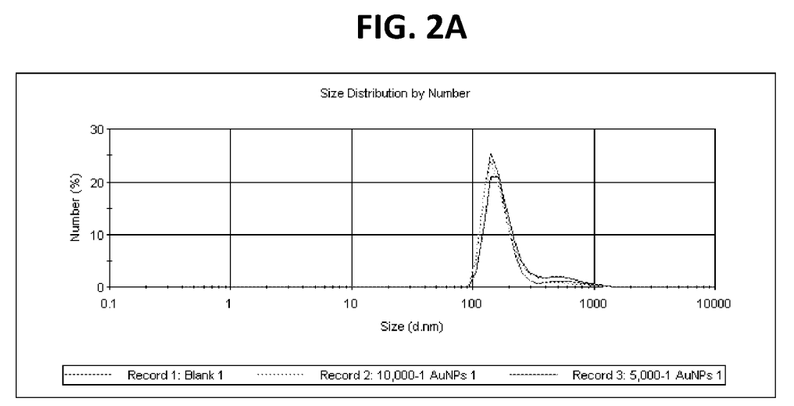
FIG. 2A is a graph showing the size distribution of liposomes produced with and without AuNPs.
Figure 2B:
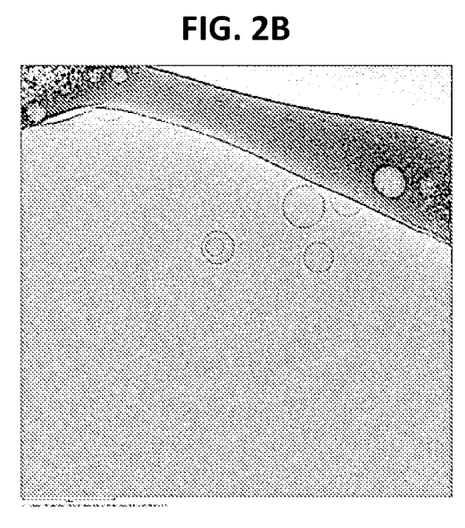
FIGS. 2B and 2C are the cryo-TEM images of the liposomes without and with AuNPs, respectively. Neither the size nor the shape of the liposomes was affected due to the incorporation of hydrophobic AuNPs into their bilayers.
Figure 2C:
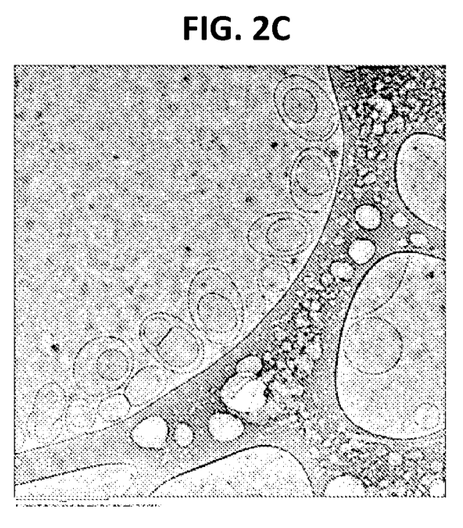

In one embodiment, liposomes were prepared by a thin film hydration method. Briefly, a chloroform solution of the cationic lipid DOTMA with or without hydrophobic AuNPs at a 10,000:1 or 5,000:1 (lipid molecules v. NPs) ratio was prepared in a sterile glass vial. A thin uniform film was then prepared by rapidly evaporating the chloroform in vacuo for 2 hours at 25° C. in order to remove the solvent. This film was then hydrated using an appropriate volume of pH 7.4 phosphate buffered saline containing eGFP-specific siRNA by vortexing for 30 seconds. The resulting dispersion was then sonicated using a bath sonicator for 30 minutes. The total lipid and siRNA concentrations in the liposomes were 1 mM and 400 nM, respectively. The size of the liposomes was measured using dynamic light scattering (Zetasizer Nano ZS, Malvern Instruments Ltd., Worcestershire, UK) and the morphology of the liposomes was determined using cryo-TEM (JEM-2100F, Jeol USA Inc., MA, USA). As shown in FIG. 2, neither the size nor the shape of the NPs-containing liposomes were significantly different from non-NPs-containing controls due to the presence of hydrophobic AuNPs in the bilayers. The size of the liposomes with and without hydrophobic AuNPs was 203-225 nm and the polydispersity index was 0.277-0.299.

Figure 3A:
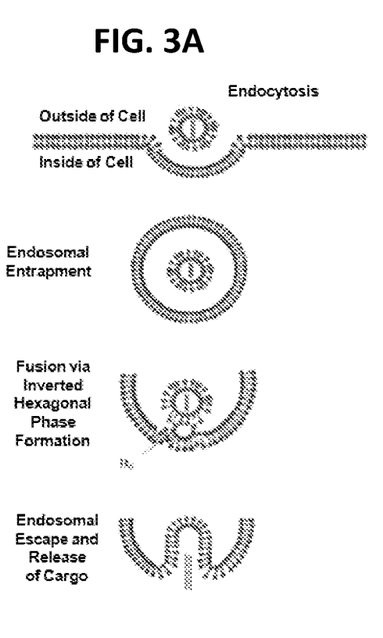
FIGS. 3A-3C are schematic presentations of hydrophobic NPs-induced liposome-endosome membrane fusion, leading to enhanced endosomal escape and improved delivery of the liposomal cargo into the cytosol. The liposomes taken inside the cell by endocytosis are entrapped in the endosomes and release their cargo into the cytosol by fusing with the endosomes (FIG. 3A). This fusion between liposomal and endosomal bilayers occurs via inverted hexagonal ($H_{II}$) phase formation that generates packing frustration in both the bilayers (FIG. 3B). The presence of hydrophobic nanoparticles relaxes this packing frustration and promotes fusion via $H_{II}$ phase formation (FIG. 3C).
Figure 3B:
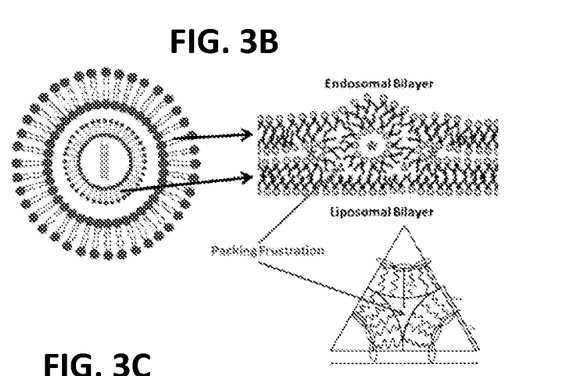
Figure 3C:
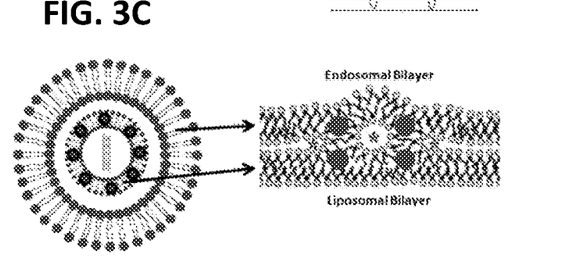

Prior to the invention described herein, the release of liposome contents into the cytosol was problematic due to the entrapment of liposomes and their contents within the endosomal compartments after endocytosis. As described herein, after the endocytosis of hydrophobic NPs-containing liposomes, the presence of the hydrophobic NPs in the liposomal bilayers promotes membrane fusion via $H_{II}$ phase formation between the liposomal and endosomal membranes by relaxing the packing frustration, thereby increasing membrane fusion and enhancing the release of the liposomal cargo into the cytosol. This mechanism of action is illustrated in FIG. 3.

Example 2

Figure 4A:
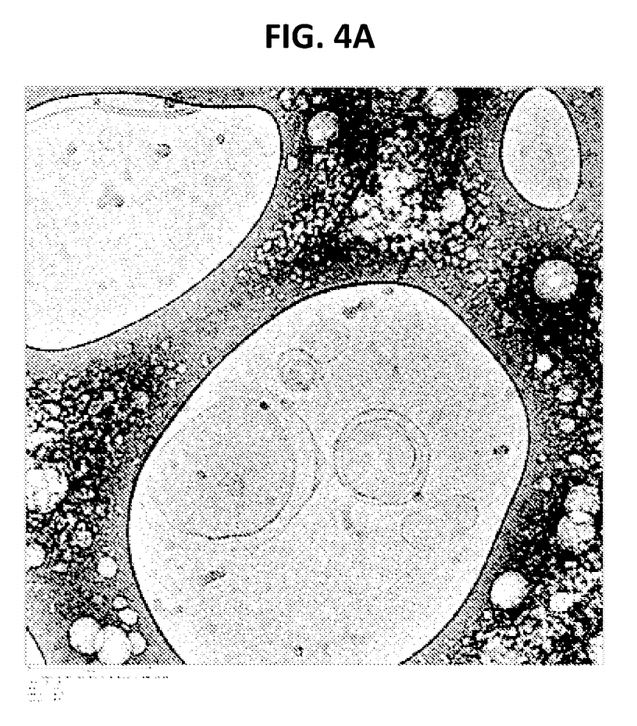
FIGS. 4A-4E provide experimental evidence of the promotion of fusion between bilayers via $H_{II}$ phase formation using hydrophobic NPs. Multilamellar vesicles (MLVs) simulating endosomal entrapment are shown in a cryo-TEM image (FIG. 4A). The change of a high field peak and a low field shoulder to a low field peak and a high field shoulder pattern at 50° C. in the $^{31}$P-NMR profile of the liposomes indicates $H_{II}$ phase transition (FIG. 4B). This change in peak pattern occurred at a lower temperature of 40° C. for the MLVs containing 2 nm hydrophobic AuNPs in their bilayers at a ratio of 10,000:1 lipid molecules: NPs (FIG. 4C) and the intensity of the low field peak was higher at the same temperature when the NP ratio was increased to 5,000:1 lipid molecules:AuNPs (FIG. 4D). The $H_{II}$ phase transition temperature was reduced to 35° C. upon the incorporation of 4 nm hydrophobic AgNPs in the bilayers of the MLVs (FIG. 4E).
Figure 4B:
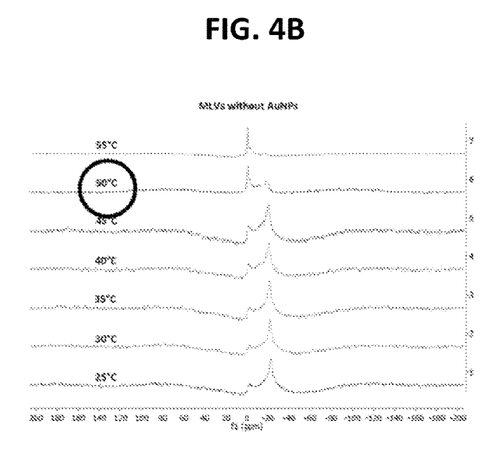
Figure 4C:
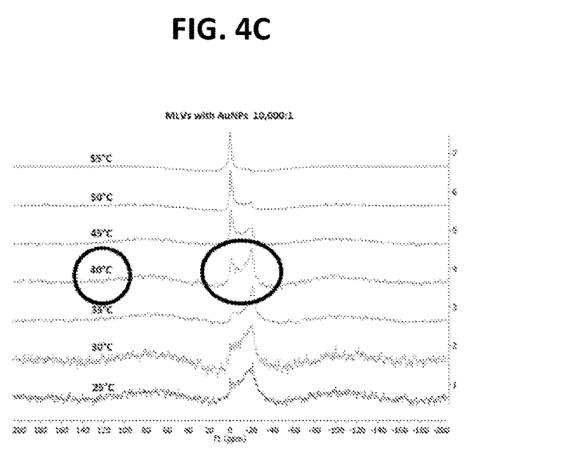
Figure 4D:
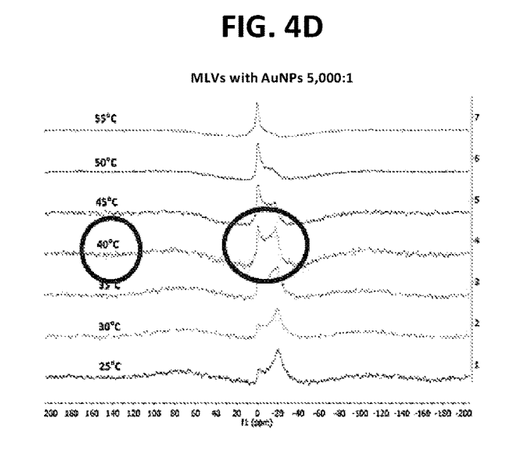
Figure 4E:
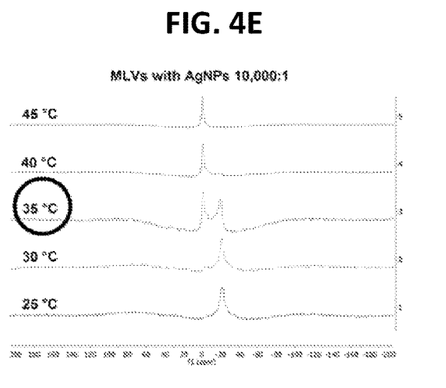

In another embodiment, MLVs were prepared by a thin film hydration method in order to study membrane fusogenicity enhancement induced by the inclusion of NPs in the membranes of these vesicles. Briefly, chloroform solutions of the cationic lipid DOTMA and the anionic lipid DPPS at an equimolar ratio with or without hydrophobic NPs at 10,000:1 or 5,000:1 (lipid molecules v. NPs) ratios were prepared in sterile glass vials. Thin uniform films were then prepared by rapidly evaporating the chloroform under vacuum for 2 hours at 25° C. in order to remove the trace solvent impurities. This film was then hydrated using an appropriate volume of citrate buffer (pH 4.5) in 10% $D_2O$ by vortexing for 30 seconds. The total lipid concentration in the resulting aqueous dispersion was 15 mM. The dispersion was then sonicated using a bath sonicator for 30 minutes. The morphology of the liposomes was assessed using cryo-TEM (JEM-2100F, Jeol USA Inc., MA, USA) and the phase transition was detected using $^{31}$P-NMR (Varian 500 MHz, Agilent Technologies, CA, USA) analysis. The enhancement in fusogenicity was determined by the reduction in the $H_{II}$ phase transition temperature. The MLVs (FIG. 4A) depict a characteristic $^{31}$P-NMR profile with a high field peak and a low field shoulder pattern, which changes to a low field peak and a high field shoulder upon transition to the $H_{II}$ phase (FIG. 4B). As illustrated in FIGS. 4B and 4C, this phase transition temperature was reduced from 50° C. to 40° C. upon incorporating 2 nm AuNPs at 10,000:1 (lipid molecules v. NPs) ratio into the bilayers. Although the phase transition temperature was not further reduced, the intensity of the low field peak was higher for vesicles containing a 5,000:1 (lipid molecules v. NPs) ratio at 40° C. for this system (FIG. 4D). In an analogous experiment, the phase transition temperature was further reduced to 35° C. upon incorporation of 4 nm AgNPs at 10,000:1 (lipid molecules v. NPs) ratio into the bilayers (FIG. 4E). Thus, the inclusion of NPs in the liposomal bilayers increased the fusogenicity of the bilayers, and this effect tended to be enhanced with an increase in concentration and size of the NPs.

Example 3

In another embodiment, liposomes were prepared using a thin film hydration method. Briefly, a chloroform solution of the cationic lipid DOTMA and the non-ionic lipid DSPC at an equimolar ratio both with and without hydrophobic NPs at 10,000:1 (lipid molecules v. NPs) ratio was prepared in a sterile glass vial. A thin uniform film was then prepared by rapidly evaporating the chloroform under vacuum for 2 hours at 25° C. in order to remove the solvent. This film was then hydrated using an appropriate volume of phosphate buffered saline with/without comprising nucleic acid (pDNA) by vortexing for 30 seconds. The resulting dispersion was then sonicated using a bath sonicator for 30 minutes. The total lipid and pDNA concentrations in the liposomes were 2 mM and 40 ng/μl, respectively.

Example 4

In a further embodiment, liposomes were prepared by a thin film hydration method. Briefly, a chloroform solution of cationic lipid DOTMA and non-ionic lipid DSPC at an equal molar ratio with/without hydrophobic NPs at 10,000:1 (lipid molecules v. NPs) ratio was prepared in a sterile glass vial. A thin uniform film was then prepared by rapidly evaporating chloroform under vacuum for 2 hours in order to remove the trace solvent impurities. This film was then hydrated using appropriate volume of phosphate buffer saline containing a polynucleotide siRNA, or without siRNA as a control, by vortexing for 30 seconds. The resulting dispersions were then sonicated using a bath sonicator for 30 minutes. The total lipid and siRNA concentrations in the liposomes were 2 mM and 400 nM, respectively.

Example 5

Figure 5A:
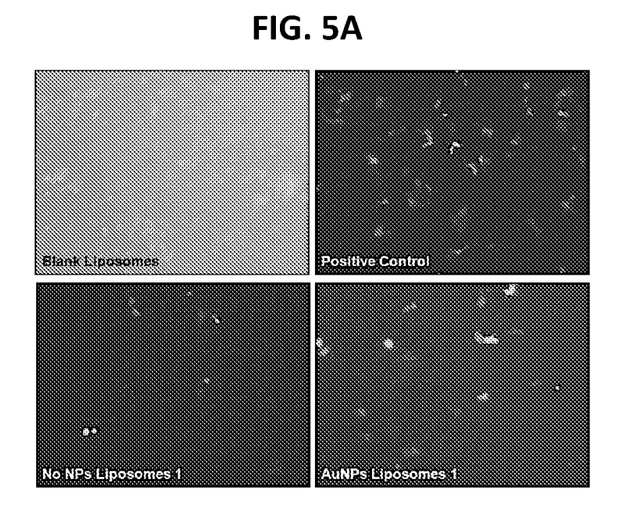
FIG. 5A is a series of fluorescence microscopic images of Huh-7 cells transfected with enhanced green fluorescence protein (eGFP), expressing pDNA delivered to the cells using either a commercial transfecting reagent (GenJet) as a positive control or using liposomes with or without 2 nm hydrophobic AuNPs in their bilayers.
Figure 5B:
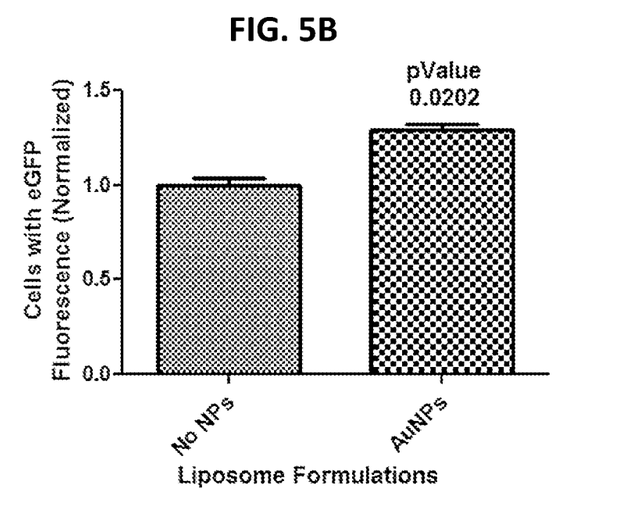
FIG. 5B is a bar chart of the flow cytometric measurement, which shows a larger number of cells with eGFP fluorescence when transfected using AuNPs-containing liposomes as compared to those transfected using liposomes without AuNPs.

In another embodiment, the enhancement in transfection efficiency due to the incorporation of hydrophobic AuNPs into liposomal bilayers was demonstrated using eGFP-expressing pDNA. Briefly, Huh-7 cells were seeded at a concentration of 4×10$^5$ cells/well into 6-well plates and transfected in the presence of OPTIMEM-1 using 100 liposomes comprising (a) eGFP-expressing pDNA at 40 ng/μl concentration encapsulated in the hydrophilic core; (b) the cationic lipid DOTMA at 1 mM concentration; (c) the non-ionic lipid DSPC at 1 mM concentration; and both with and without (d) hydrophobic AuNPs at a 10,000:1 (lipid molecules v. NPs) ratio. After 48 hours of transfection incubation, the eGFP fluorescence in the cells was observed under a fluorescence microscope (Eclipse TE2000-E, Nikon Instruments Inc., NY, USA) using a FITC filter and the cells expressing eGFP fluorescence were counted using a Flow Cytometer (BD FACSVerse™, BD Biosciences, CA, USA). As shown in FIG. 5, the number of cells showing eGFP fluorescence was 28% higher when transfected using AuNPs-containing liposomes as compared to those transfected using liposomes without AuNPs.

Figure 6A:
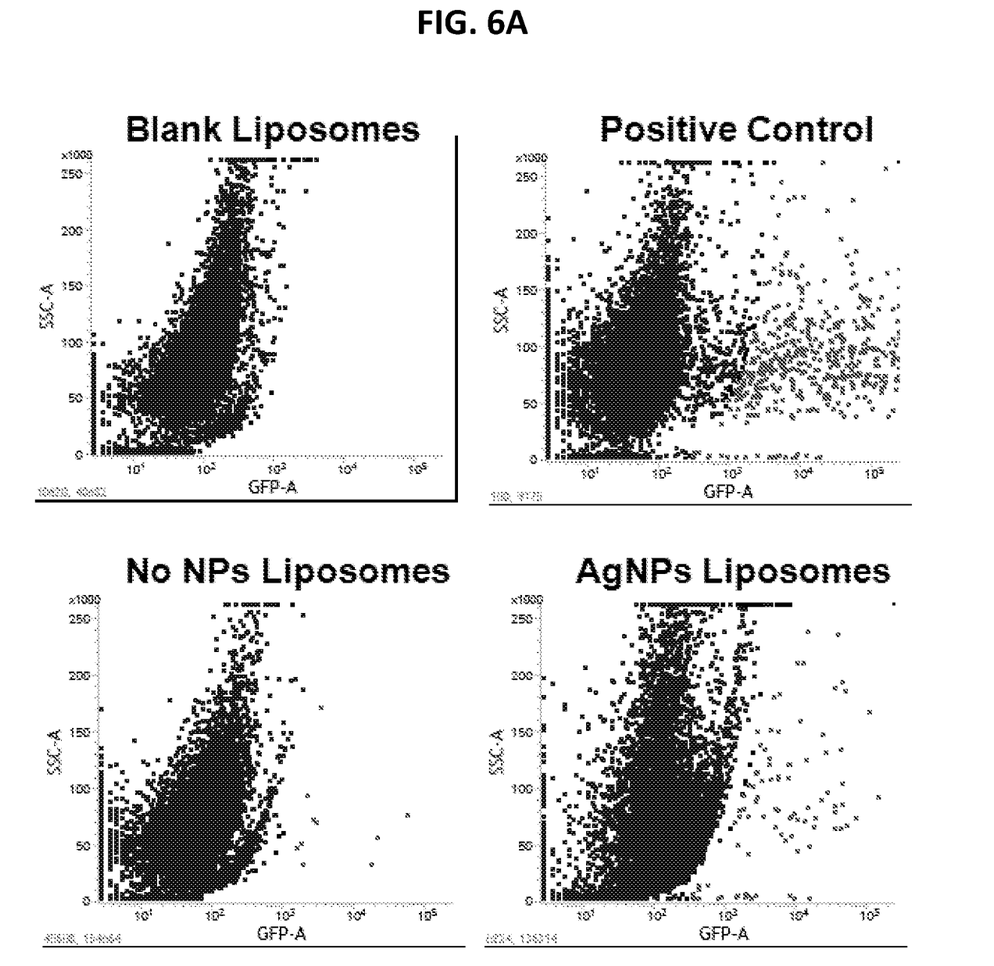
FIG. 6A is a series of dot plots obtained using flow cytometric analysis of Huh-7 cells transfected with eGFP, expressing pDNA delivered to the cells using either a commercial transfecting reagent (GenJet) as a positive control or using liposomes with or without 4 nm hydrophobic AgNPs in their bilayers.
Figure 6B:
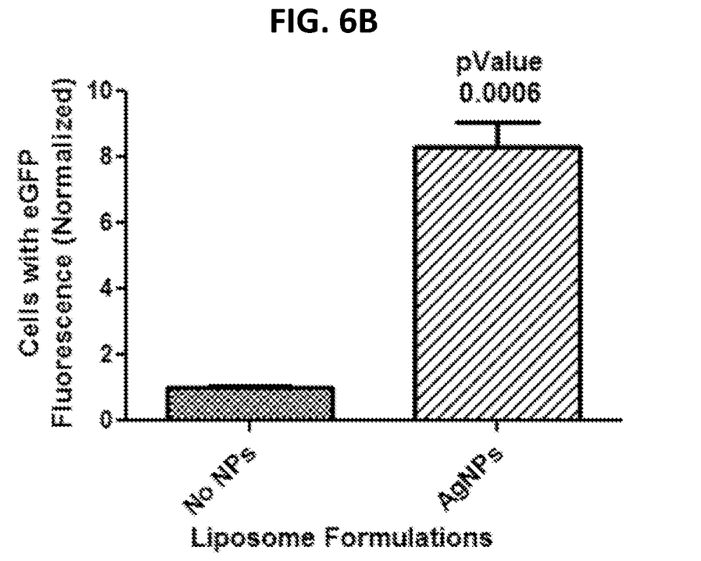
FIG. 6B is a bar chart of the flow cytometric measurement, which shows a larger number of cells with eGFP fluorescence when transfected using AgNPs-containing liposomes as compared to those transfected using liposomes without AgNPs.

For example, Huh-7 cells were seeded in 12-well plates at a concentration of 2×10$^5$ cells/well and transfected in the presence of DMEM using 50 μl/well liposomes comprising (a) eGFP expressing pDNA at 40 ng/μl concentration encapsulated in the hydrophilic core; (b) a cationic lipid DOTMA at 1 mM concentration; (c) a non-ionic lipid DSPC at 1 mM concentration; and both with and without (d) hydrophobic AgNPs at a 10,000:1 lipid molecules:NPs ratio. After 48 hours of transfection incubation, the cells expressing eGFP fluorescence were counted using a Flow Cytometer (BD FACSVerse™, BD Biosciences, CA, USA). As shown in FIG. 6, the number of cells showing eGFP fluorescence was 8-fold higher when transfected using AgNPs-containing liposomes as compared to cells transfected using liposomes without AgNPs.

Example 6

Figure 7A:
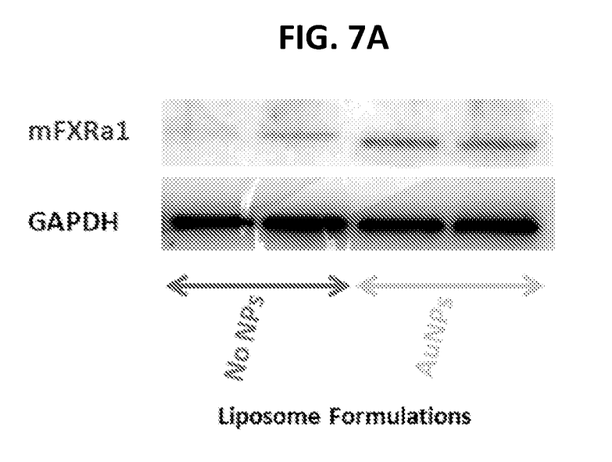
FIG. 7A is an image of the Western blot analysis showing expression of mFXRa1 protein normalized against the house-keeping gene protein GAPDH in Huh-7 cells transfected with mFXRa1, expressing pDNA delivered to the cells using liposomes with or without 2 nm hydrophobic AuNPs in their bilayers.
Figure 7B:
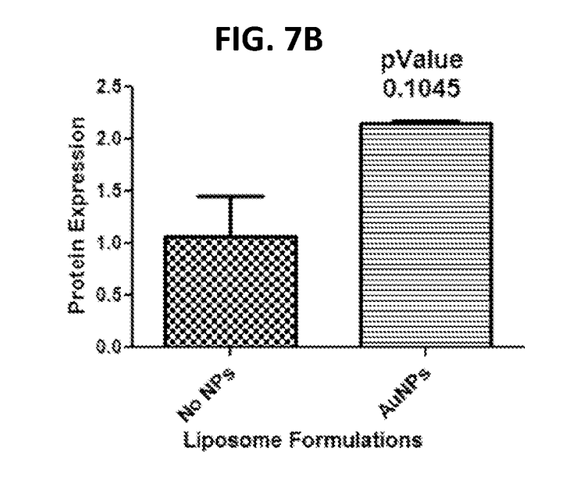
FIG. 7B is a bar plot of the quantification of mFXRa1 protein, which is significantly higher in the cells transfected using AuNPs-containing liposomes as compared to those transfected using liposomes without AuNPs.

In another embodiment, the enhancement in pDNA transfection efficiency resulting from the incorporation of hydrophobic AuNPs into the liposomal bilayers was demonstrated using mFXRa1 protein expressing pDNA. Briefly, Huh-7 cells were seeded in 6 well plates at a concentration of 4×10$^5$ cells/well and transfected in the presence of OPTIMEM-1 using 100 μl/well liposomes comprising (a) mFXRa1 expressing pDNA at 40 ng/μl concentration encapsulated in the hydrophilic core; (b) the cationic lipid DOTMA at 1 mM concentration; (c) the non-ionic lipid DSPC at 1 mM concentration; both with and without (d) hydrophobic AuNPs at a 10,000:1 lipid molecules:NPs ratio. After 48 hours of transfection, the protein expression was determined using the Western blot method by normalizing its expression against the housekeeping gene product GAPDH. As shown in FIG. 7, mFXRa1 protein expression was higher in cells transfected using AuNPs-containing liposomes as compared to cells transfected using liposomes without AuNPs.

Example 7

Figure 8:
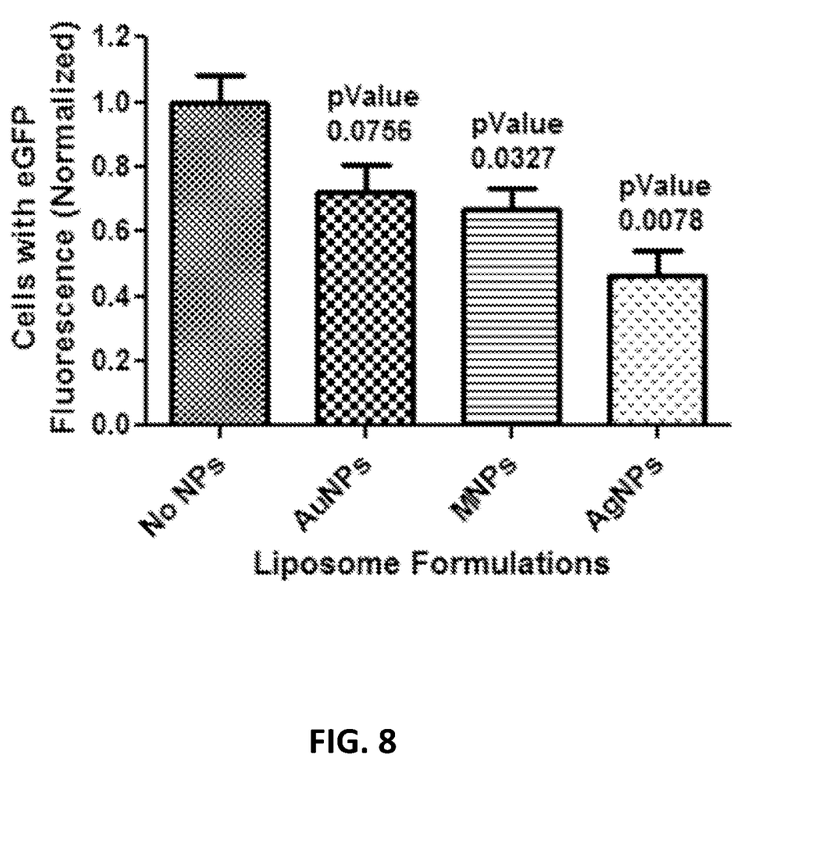
FIG. 8 is a bar chart of the flow cytometric measurement of Huh-7 cells transfected with eGFP, expressing pDNA using a commercial transfecting reagent (GenJet). When followed by eGFP-specific silencing siRNA transfection using liposomes, a significantly lower number of cells displayed eGFP fluorescence when transfected using hydrophobic NPs-containing liposomes (silver, gold, or iron) as compared to those transfected using liposomes without NPs.

In another embodiment, Huh-7 cells were seeded in 12 well plates at a concentration of 2×10$^5$ cells/well in the presence of OPTIMEM-1 and transfected with eGFP expressing pDNA at a concentration of 2 μg/well using the commercial transfection agent GenJet. The medium was replaced after 12 hours and the cells were then transfected using 50 μl/well liposomes comprising (a) eGFP specific silencing siRNA at a concentration of 400 nM encapsulated in the hydrophilic core; (b) the cationic lipid DOTMA at 1 mM concentration; (c) the non-ionic lipid DSPC at 1 mM concentration; both with and without (d) hydrophobic NPs at a 10,000:1 (lipid molecules v. NPs) ratio. After 48 hours of transfection incubation, the cells expressing eGFP fluorescence were counted using a Flow Cytometer (BD FACS-Verse™, BD Biosciences, CA, USA). As shown in FIG. 8, the number of cells showing eGFP fluorescence was lower when transfected with the gene silencing siRNA using liposomes containing hydrophobic NPs of various types and sizes (silver, gold, and iron; 4, 2, and 5 nm in) as compared to the number of cells transfected using liposomes without NPs. The iron (magnetic) nanoparticles (labeled as "MNPs", commercially available from Ocean Nanotech (San Diego, Calif., USA) used here were coated with oleic acid, a type of fatty acid.

All references cited herein are incorporated herein by reference in their entirety to the extent allowed by applicable laws and for all purposes to the same extent as if each individual publication or patent or patent application is specifically and individually indicated to be incorporated by reference in its entirety for all purposes. To the extent publications and patents or patent applications incorporated by reference contradict the disclosure including definitions contained in the present specification, the specification is intended to supersede and/or take precedence over any such contradictory material.

What is claimed is:

1. A method of delivering a payload into a biological subject, said method comprising the steps of:
    (a) providing a liposome comprising a lipid bilayer defining a hollow center encapsulating a payload, said lipid bilayer comprising one or more cationic lipids, one or more non-ionic lipids, and nanoparticles embedded therein where each nanoparticle comprises a metal core covalently derivatized with hydrophobic groups on its surface, and wherein said payload comprises a biologic therapeutic consisting of polynucleotides;
    (b) introducing said liposome into a cellular endosome through endocytosis in a biological subject, said embedded hydrophobic nanoparticles enhancing inverted hexagonal phase formation and fusogenicity between said liposomal lipid bilayer and an endosomal lipid bilayer of a cellular endosome; and
    (c) delivering said payload outside of said endosome.

2. The method of claim 1, wherein said polynucleotides are selected from the group consisting of ribonucleic acid (RNA), deoxyribonucleic acid (DNA), messenger RNA (mRNA), interfering RNA (iRNA), small interfering RNA (siRNA), micro RNA (miRNA), plasmid DNA (pDNA), and mixtures thereof.

3. The method of claim 1, wherein said hydrophobic groups on said nanoparticle surfaces derive from fatty acids, or alkyl thiols.

4. The method of claim 1, wherein said metal nanoparticle core is made of a metal selected from the group consisting of iron, gold, silver, chromium, manganese, magnesium, titanium, cobalt, nickel, copper, cadmium, zinc, neodymium, samarium, ytterbium, gadolinium, vanadium, terbium, dysprosium, holmium, erbium, aluminum, rhenium, platinum, palladium, and mixtures thereof.

5. The method of claim 1, wherein said nanoparticles are embedded in said one or more lipid bilayers at a concentration ranging from about 1,000 to about 20,000 lipid molecules for each nanoparticle.

6. A method of delivering a payload into a biological subject, said method comprising the steps of:
    (a) providing a liposome comprising a lipid bilayer defining a hollow center encapsulating a payload comprising a biologic therapeutic consisting of polynucleotides, said lipid bilayer comprising one or more cationic lipids, one or more non-ionic lipids, and nanoparticles embedded therein where each nanoparticle comprises a metal core covalently derivatized with hydrophobic groups derived from a fatty acid on its surface;
    (b) introducing said liposome into a cellular endosome through endocytosis in a biological subject, said embedded hydrophobic nanoparticles enhancing inverted hexagonal phase formation and fusogenicity between said liposomal lipid bilayer and an endosomal lipid bilayer of a cellular endosome; and
    (c) delivering said payload outside of said endosome.

7. A method of delivering a payload into a biological subject, said method comprising the steps of:
    (a) providing a liposome comprising a lipid bilayer defining a hollow center encapsulating a payload comprising a biologic therapeutic consisting of polynucleotides, said lipid bilayer comprising one or more cationic lipids, one or more non-ionic lipids, and nanoparticles embedded therein where each nanoparticle comprises a metal core covalently derivatized with hydrophobic groups derived from an alkyl thiol on its surface;
    (b) introducing said liposome into a cellular endosome through endocytosis in a biological subject, said embedded hydrophobic nanoparticles enhancing inverted hexagonal phase formation and fusogenicity between said liposomal lipid bilayer and an endosomal lipid bilayer of a cellular endosome; and
    (c) delivering said payload outside of said endosome.

8. The method of claim 1 wherein the enhancing step enables a greater amount of payload to be released under normal physiological conditions when compared with a standard liposome, said standard liposome not comprising said nanoparticles but otherwise identical to said liposome.

9. The method of claim 8 wherein the greater amount is greater than or equal to 10% more.

10. The method of claim 9 wherein the greater amount is greater than 900%.

11. The method of claim 1 wherein the enhancing step comprises reducing a phase transition temperature of the inverted hexagonal phase formation from about 1° C. to about 20° C.

12. The method of claim 6 wherein the enhancing step enables a greater amount of payload to be released under normal physiological conditions when compared with a standard liposome, said standard liposome not comprising said nanoparticles but otherwise identical to said liposome.

13. The method of claim 12 wherein the greater amount is greater than or equal to 10% more.

14. The method of claim 13 wherein the greater amount is greater than 900%.

15. The method of claim 6 wherein the enhancing step comprises reducing a phase transition temperature of the inverted hexagonal phase formation from about 1° C. to about 20° C.

16. The method of claim 7 wherein the enhancing step enables a greater amount of payload to be released under normal physiological conditions when compared with a standard liposome, said standard liposome not comprising said nanoparticles but otherwise identical to said liposome.

17. The method of claim 16 wherein the greater amount is greater than or equal to 10% more.

18. The method of claim 17 wherein the greater amount is greater than 900%.

19. The method of claim 7 wherein the enhancing step comprises reducing a phase transition temperature of the inverted hexagonal phase formation from about 1° C. to about 20° C.

20. A method of delivering a payload into a biological subject, said method comprising the steps of:
- (a) providing a liposome comprising a lipid bilayer defining a hollow center encapsulating a payload comprising a biologic therapeutic consisting of polynucleotides, said lipid bilayer comprising (1) one or more cationic lipids, (2) one or more non-ionic lipids, (3) one or more anionic lipids, and (4) nanoparticles where each nanoparticle comprises a gold or silver core covalently derivatized with a hydrophobic group derived from an alkyl thiol on its surface, wherein more than 10 mol % of total lipids in said lipid bilayer are cationic, from 0.1 mol % to 90 mol % of the total lipids are non-ionic, from 0.1 mol % to 90 mol % of the total lipids are anionic, and wherein said nanoparticles are incorporated into the lipid bilayer at a ratio ranging from about 1,000:1 to about 20,000:1 (lipid molecules to nanoparticles);
- (b) introducing said liposome into a cellular endosome through endocytosis in a biological subject, said embedded hydrophobic nanoparticles enhancing inverted hexagonal phase formation and fusogenicity between said liposomal lipid bilayer and an endosomal lipid bilayer of a cellular endosome by reducing a phase transition temperature of the inverted hexagonal phase formation from about 1° C. to about 20° C.; and
- (c) delivering said payload outside of said endosome.

* * * * *

UNITED STATES PATENT AND TRADEMARK OFFICE
CERTIFICATE OF CORRECTION

PATENT NO. : 11,433,026 B2
APPLICATION NO. : 15/943538
DATED : September 6, 2022
INVENTOR(S) : Sarode et al.

It is certified that error appears in the above-identified patent and that said Letters Patent is hereby corrected as shown below:

On the Title Page

There should be a section under the heading "Related U.S. Application Data" with information as follows:
(60) Provisional application No. 62/479,753, filed on Mar. 31, 2017.

Signed and Sealed this
Third Day of January, 2023

Katherine Kelly Vidal
*Director of the United States Patent and Trademark Office*